United States Patent
Kar et al.

(10) Patent No.: US 9,447,201 B2
(45) Date of Patent: Sep. 20, 2016

(54) POLYMERIZATION INHIBITOR COMPOSITION AND METHOD OF INHIBITING POLYMERIZATION OF DISTILLABLE MONOMERS

(75) Inventors: Kishore K. Kar, Midland, MI (US); Michael D. Cloeter, Lake Jackson, TX (US); Olan Stanley Fruchey, Hurricane, WV (US); Richard S. Harner, Midland, MI (US); Krzysztof Matyjaszewski, Pittsburgh, PA (US); Renaud Nicolay, Clamart (FR); Jaroslav Mosnáček, Bratislava (SK)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 1152 days.

(21) Appl. No.: 13/147,733

(22) PCT Filed: Feb. 18, 2010

(86) PCT No.: PCT/US2010/024509
§ 371 (c)(1),
(2), (4) Date: Aug. 3, 2011

(87) PCT Pub. No.: WO2010/096512
PCT Pub. Date: Aug. 26, 2010

(65) Prior Publication Data
US 2011/0290635 A1    Dec. 1, 2011

Related U.S. Application Data

(60) Provisional application No. 61/153,345, filed on Feb. 18, 2009.

(51) Int. Cl.
*C07C 51/50* (2006.01)
*C07C 67/62* (2006.01)
*C08F 2/42* (2006.01)
*C07C 51/44* (2006.01)
*C08F 2/40* (2006.01)

(52) U.S. Cl.
CPC ............... *C08F 2/42* (2013.01); *C07C 51/44* (2013.01); *C07C 51/50* (2013.01); *C08F 2/40* (2013.01)

(58) Field of Classification Search
CPC .............................. C07C 51/50; C07C 67/62
USPC ......................................... 252/182.29; 203/8
See application file for complete search history.

(56) References Cited

U.S. PATENT DOCUMENTS

| 3,397,232 A | 8/1968 | Takagi et al. |
| 3,699,081 A * | 10/1972 | Iwashita et al. ............... 564/4 |
| 4,210,493 A | 7/1980 | Stewart et al. |
| 5,272,231 A | 12/1993 | Campbell et al. |
| 5,504,243 A | 4/1996 | Sakamoto et al. |
| 5,888,356 A | 3/1999 | Keil et al. |
| 6,518,374 B1 * | 2/2003 | Aichinger et al. ............ 526/84 |
| 7,241,915 B2 | 7/2007 | Ishida et al. |
| 7,306,204 B2 | 12/2007 | Thiel et al. |
| 7,319,167 B2 | 1/2008 | Nakahara et al. |
| 7,319,168 B2 | 1/2008 | Sanada |
| 7,388,109 B2 | 6/2008 | Machhammer et al. |
| 2003/0176725 A1 | 9/2003 | Ishida et al. |
| 2009/0253934 A1 | 10/2009 | Ho et al. |
| 2009/0299090 A1 * | 12/2009 | Briegel ................. C07C 51/46 560/218 |
| 2009/0306370 A1 | 12/2009 | Wakita |

FOREIGN PATENT DOCUMENTS

| JP | S50-64214 A | 5/1975 |
| JP | 2002543223 A | 12/2002 |
| JP | 2003267929 A | 9/2003 |
| JP | 2004107279 A | 4/2004 |
| JP | 2007077138 A | 3/2007 |

OTHER PUBLICATIONS

English abstract of Aoki et al., JP 01-226858A (1988).*
Coleman et al., "Nitrosobenzene", Organic Syntheses, Coll. vol. 3, p. 668 (1955); vol. 25, p. 80 (1945).
Robinson et al., Elements of Fractional Distillation, 4th Ed. (1950), Chapters 1-4, p. 3-100.
Favre et al., "Selective Reduction of Nitrobenzene to Nitrosobenzene on Oxidic Catalysts", Catalysis Letters 1 (1988) 457-460.
English language translation for JPS50-64214 A, 5 pages.
English language abstract and machine assisted translation for JP2004-107279 A extracted from https://www4.j•platpat.inpit.go.jp database on Aug. 10, 2015, 15 pages.
English translation of Notice of Preliminary Rejection office action summary for Korean patent application No. 2011-7019186 pursuant to PCT/US2010/024509, 9 pages.

* cited by examiner

*Primary Examiner* — Peter F Godenschwager
(74) *Attorney, Agent, or Firm* — Warner Norcross & Judd LLP

(57) ABSTRACT

The present invention relates to a polymerization inhibitor composition and a method of inhibiting polymerization of distillable monomers in liquid and evaporated/condensed phases with the polymerization inhibitor composition. The polymerization inhibitor composition is useful for inhibiting polymerization of the distillable monomers during manufacture, purification (e.g., distillation), handling, and storage thereof.

20 Claims, 1 Drawing Sheet

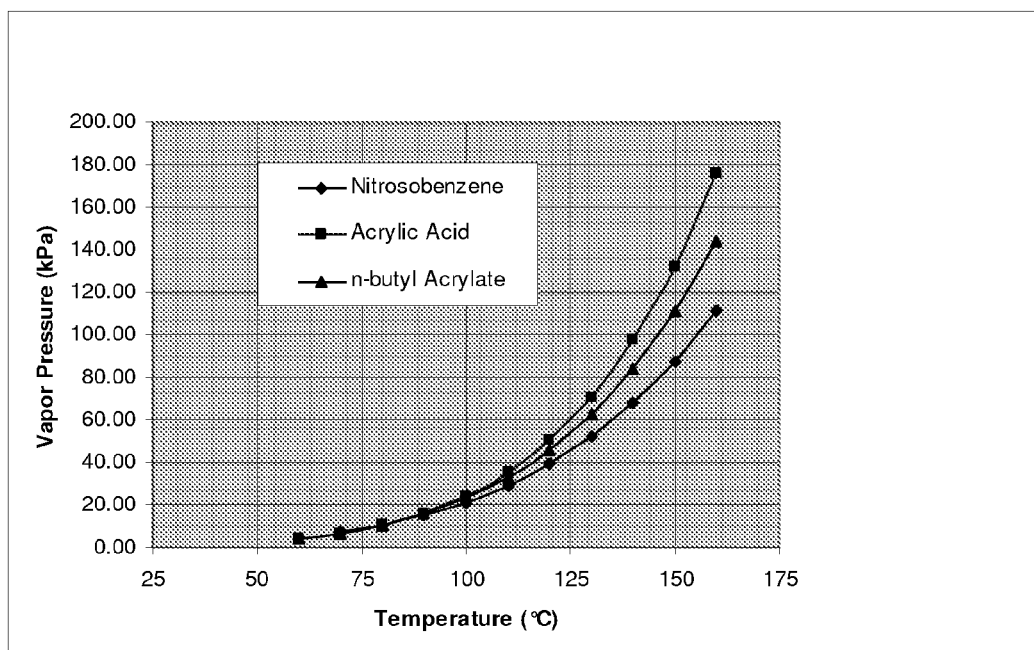
PRIOR ART

POLYMERIZATION INHIBITOR COMPOSITION AND METHOD OF INHIBITING POLYMERIZATION OF DISTILLABLE MONOMERS

CROSS REFERENCE TO RELATED APPLICATIONS

This is a §371 application of PCT International Patent Application Number PCT/US2010/024509 filed Feb. 18, 2010, and claims priority from provisional application Ser. No. 61/153,345 filed Feb. 18, 2009, each of which is incorporated herein by reference in its entirety.

BACKGROUND OF THE INVENTION

1. Field of the Invention

The present invention relates to a polymerization inhibitor composition and a method of inhibiting polymerization of distillable monomers in liquid and evaporated/condensed phases with the polymerization inhibitor composition. The polymerization inhibitor composition is useful for inhibiting polymerization of the distillable monomers during manufacture, purification (e.g., distillation), handling, and storage thereof.

2. Description of the Related Art

Acrylic acid-type monomers include monomers having a structural fragment,

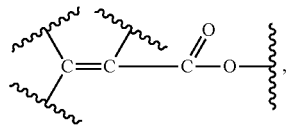 [SMILES: *OC(=O)C(*)=C(*)*]

wherein

represent portions of covalent bonds. The acrylic acid-type monomers are widely used in chemical industry to prepare polyacrylate-type polymers (e.g., poly(acrylic acid)s and poly(methacrylic acids)), which are useful as, among other things, additives (e.g., for use in rubbers, coatings and adhesives) and ingredients in fibers and other articles. A major problem with the acrylic acid-type monomers is premature polymerization. In the absence of sufficient amounts of polymerization inhibitors, acrylic acid-type monomers undesirably polymerize during manufacture, purification, handling, and storage operations.

An especially difficult problem has been premature polymerization of evaporated and condensed acrylic acid-type monomers in headspaces of vessels and piping having headspaces. For example, purification by reduced pressure distillation comprises distilling an acrylic acid-type monomer from a distillation pot having a volume of monomer and headspace and through a distillation column (headspace). During distillation a portion of the acrylic acid-type monomer evaporates and eventually condenses on certain structures (i.e., "cold" spots) within the column. If the condensed monomer lacks a polymerization inhibitor, it will polymerize and thereby foul structures in the column, especially structures that are more not in direct liquid communication with the distillation pot and from column zone receiving splashes therefrom. Eventually the distillation operation must be shut down and the fouled column cleaned, an expensive and time-consuming maintenance operation. To inhibit polymerization, the chemical industry has added polymerization inhibitors to batches of the monomers before subjecting the batches to these operations or, less desirably, physically added such polymerization inhibitors during the operations, but with less than desirable results.

For example, some such prior art polymerization inhibitors are known from U.S. Pat. No. 4,210,493, which mentions nitrosobenzene and 4-nitrosophenol, among others and optionally physically adding the same to plates in distillation columns during distillations; U.S. Pat. No. 5,272,231, which mentions nitric oxide, among others; U.S. Pat. No. 5,504,243, which mentions certain N-oxyl compounds and certain nitroso compounds, among others; U.S. Pat. No. 5,888,356, which mentions certain N-oxyl compounds and certain nitroso compounds; U.S. Pat. No. 7,241,915 B2; U.S. Pat. No. 7,319,167 B2, which mentions a method of physically adding certain such polymerization inhibitors to a condensate or a reflux liquid during distillation; U.S. Pat. No. 7,319,168 B2; and U.S. Pat. No. 7,388,109 B2. Also see WO 2009/032427. But such prior art polymerization inhibitors are unsatisfactory for evaporating and condensing with, and thereby inhibiting polymerization of condensates of, acrylic acid-type monomers on the structures in distillation columns. Either they are insufficiently volatile to evaporate to the structures or they are overly volatile and do not condense on the structures with condensed acrylic acid-type monomers.

The overly-volatile prior art polymerization inhibitors comprise compounds that readily evaporate at vapor pressures and temperatures suitable for distilling acrylic acid-type monomers, but either do not condense with condensed acrylic acid-type monomers on the structures in the columns or condense in amounts below those required to effectively inhibit polymerization of the acrylic acid-type monomer condensates. Examples of the overly-volatile polymerization inhibitors are gases such as oxygen gas and nitric oxide gas, which have been used to inhibit vapor-phase polymerization but do not condense in such reduced pressure distillation columns.

The insufficiently-volatile prior art polymerization inhibitors comprise two types of inhibitors. One such type of insufficiently-volatile polymerization inhibitor comprises compounds that, at vapor pressures and temperatures suitable for distilling acrylic acid-type monomers, are substantially captive to the distillation pot batch of monomer to which they are added. The other type of insufficiently-volatile polymerization inhibitor comprises compounds that, before evaporating, react in situ to form captive derivative polymerization inhibitor compounds. Examples of the former type of insufficiently-volatile polymerization inhibitor are 4-nitrosophenol, 2-methyl-4-nitrosophenol, N-nitrosodiphenylamine and salts thereof, N-nitrosophenylhydroxyamine and salts thereof, and phenylnitroxide. An example of the latter type of insufficiently-volatile polymerization inhibitor is a lone inhibitor nitrosobenzene, which, before evaporating, reacts in situ during such distillations to form phenylnitroxide. Substantial amounts of the insufficiently-volatile polymerization inhibitors, or insufficiently-volatile derivatives of polymerization inhibitors such as phenylnitroxide, remain in distillation pots during such reduced pressure distillation operations and essentially do not inhibit polymerization of the evaporated and condensed acrylic acid-type monomers on the structures in the columns.

The chemical industry desires superior polymerization inhibitor compositions comprising a captive polymerization inhibitor and a fugitive polymerization inhibitor each independently capable of inhibiting polymerization of distillable monomers (e.g., acrylic acid-type monomers and other olefinic monomers) in vessels (e.g., distillation pots) and piping and the fugitive polymerization inhibitor preferably further capable of evaporating into headspaces in the vessels and piping and into distillation columns, condensing in a polymerization inhibiting amount with the distillable monomers, and inhibiting polymerization of the evaporated and condensed distillable monomers on structures in the headspaces (e.g., distillation columns), including structures distal from unevaporated acrylic acid-type monomers remaining in the vessels or pipes.

BRIEF SUMMARY OF THE INVENTION

In a first embodiment, the present invention provides a monomer polymerization inhibitor composition ("composition") comprising a captive polymerization inhibitor and a fugitive polymerization inhibitor, wherein: the captive polymerization inhibitor and the fugitive polymerization inhibitor are different and not interconvertible between one another; each of the fugitive polymerization inhibitor and the captive polymerization inhibitor independently is characterizable as being an inhibitor of polymerization of a same distillable monomer; and the fugitive polymerization inhibitor is characterizable as being capable of evaporating with the distillable monomer from a first location and condensing with the distillable monomer at a second location that is different than the first location during distillation of the distillable monomer.

In some aspects of the first embodiment the fugitive polymerization inhibitor and the captive polymerization inhibitor are characterizable as being inhibitors of a distillable monomer that is an olefinic monomer or a free-radical polymerizable monomer. An example of the olefinic monomer is an acrylic acid-type monomer of formula (M):

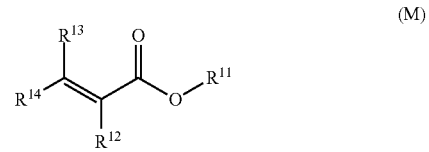

wherein $R^{11}$ is hydrogen or $(C_1-C_{18})$alkyl and each of $R^{12}$ to $R^{14}$ independently is hydrogen or $(C_1-C_8)$alkyl.

In a second embodiment, the present invention provides a method of inhibiting polymerization of a distillable monomer during a distillation thereof, the method comprising steps of: (a) contacting together the invention composition of the first embodiment and an amount of a distillable monomer to give a first mixture thereof at a first location (e.g., a distillation vessel), wherein the composition comprises a first polymerization inhibiting amount of the fugitive polymerization inhibitor and an inhibiting amount of the captive polymerization inhibitor; (b) evaporating from the first location at least some of the distillable monomer and at least some of the fugitive polymerization inhibitor to respectively give an evaporated distillable monomer and an evaporated fugitive polymerization inhibitor; and (c) condensing together at least some of the evaporated distillable monomer and at least some of the evaporated fugitive polymerization inhibitor to give a condensate mixture thereof at a second location that is different than and in fluid communication with the first location, wherein the condensate mixture comprises a mixture of some of the amount of the distillable monomer and a second polymerization inhibiting amount of the fugitive polymerization inhibitor; wherein polymerization of the distillable monomer at the second location is inhibited by the second polymerization inhibiting amount of the fugitive polymerization inhibitor; and in and under conditions of distilling steps (b) and (c), the fugitive polymerization inhibitor has a vapor pressure or relative volatility distillation performance compatible with a vapor pressure or relative volatility distillation performance of the distillable monomer. The liquid mixture and the condensate mixture are different.

In some aspects of the second embodiment the distillable monomer is an olefinic monomer or a free-radical polymerizable monomer and the captive and fugitive polymerization inhibitors are each inhibitors of polymerization thereof. In some embodiments the olefinic monomer is an acrylic acid-type monomer of formula (M):

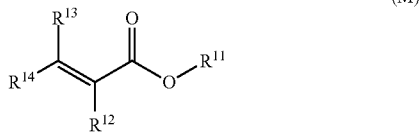

wherein $R^{11}$ is hydrogen or $(C_1-C_{18})$alkyl and each of $R^{12}$ to $R^{14}$ independently is hydrogen or $(C_1-C_8)$alkyl. In this embodiment the condensate mixture comprises an evaporated and condensed acrylic acid-type monomer of formula (M) and the second polymerization inhibiting amount of the evaporated and condensed fugitive polymerization inhibitor thereof.

The invention composition of the first embodiment is one that is capable of functioning in the method of the second embodiment. Preferably the invention composition is capable of functioning in such a way that should the invention composition be employed in a distillation of the distillable monomer from a distillation vessel (e.g., distillation pot), the captive polymerization inhibitor would essentially remain in (i.e., would not distill out of) the distillation vessel and at least a polymerization inhibiting amount portion of the fugitive polymerization inhibitor would distill with the distillable monomer. See, for example, the second embodiment.

The composition of the first embodiment is useful in manufacture, purification, handling, and storage of distillable monomers (e.g., acrylic acid-type monomers) as an inhibitor of polymerization of the distillable monomers in, for example, vessels and piping. At least preferred compositions (i.e., compatible, performance matched compositions as described later) of the first embodiment are further useful as inhibitors of distal-sited polymerization of evaporated and condensed distillable monomers on structures, including distal structures, in the headspaces of, for example, vessels and piping, and in columns, by way of the fugitive polymerization inhibitor. The captive polymerization inhibitors preferably also inhibit in situ conversion (e.g., conversion in a distillation pot), if any, of the fugitive polymerization inhibitors to other captive polymerization inhibitors. The method of the second embodiment provides steps for the captive polymerization inhibitor inhibiting polymerization of a distillable monomer (e.g., acrylic acid-type monomer) in situ and for at least some of the fugitive polymerization inhibitor evaporating and then condensing with evaporated distillable monomer at distal structures, where the evaporated and condensed fugitive polymerization inhibitor inhibits polymerization of the evaporated and condensed distillable monomer at the distal structures, all as described for the second embodiment. Such steps are not possible in a non-invention method employing a captive polymerization inhibitor alone or a fugitive polymerization inhibitor alone, including a fugitive polymerization inhibitor that, before evaporating, reacts in situ to form a captive derivative polymerization inhibitor compound.

Additional embodiments are described in accompanying drawing(s) and the remainder of the specification.

BRIEF DESCRIPTION OF THE DRAWING(S)

Some embodiments of the present invention are described herein in relation to the accompanying drawings, which will at least assist in illustrating various features of the embodiments.

FIG. 1 is a graphical plot of elevated temperature versus liquid vapor pressure data for nitrosobenzene, acrylic acid, and normal-butyl acrylate.

DETAILED DESCRIPTION OF THE INVENTION

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, headings (e.g., "Definitions") are used for convenience and are not meant, and should not be used, to limit scope of the present disclosure in any way.

In the present application, any lower limit of a range of numbers, or any preferred lower limit of the range, may be combined with any upper limit of the range, or any preferred upper limit of the range, to define a preferred aspect or embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

In an event where there is a conflict between a compound name and its structure, the structure controls.

In an event where there is a conflict between a unit value that is recited without parentheses, e.g., 2 inches, and a corresponding unit value that is parenthetically recited, e.g., (5 centimeters), the unit value recited without parentheses controls.

Definitions

As used herein, "a," "an," "the," "at least one," and "one or more" are used interchangeably. In any aspect or embodiment of the instant invention described herein, the open-ended terms "comprising," "comprises," and the like (which are synonymous with "including," "having," and "characterized by") may be replaced by the respective partially closed phrases "consisting essentially of," "consists essentially of," and the like or the respective closed phrases "consisting of," "consists of," and the like. In the present application, when referring to a preceding list of elements (e.g., ingredients), the phrases "mixture thereof," "combination thereof," and the like mean any two or more, including all, of the listed elements. The term "or" used in a listing of members, unless stated otherwise, refers to the listed members individually as well as in any combination.

The term "$(C_1-C_{18})$alkyl" means a saturated straight or branched hydrocarbon radical of from 1 to 18 carbon atoms that is unsubstituted. Examples of $(C_1-C_{18})$alkyl are $(C_9-C_{18})$alkyl (e.g., a $(C_{18})$alkyl such as $CH_3(CH_2)_{17}$—) and $(C_1-C_8)$alkyl, which includes $(C_1-C_3)$alkyl, including methyl, ethyl, 1-propyl, and 2-propyl; and $(C_4-C_8)$alkyl, including 1-butyl (also known as normal-butyl or n-butyl), 2-butyl, 2-methylpropyl, 1,1-dimethylethyl, 1-pentyl, 1-hexyl, 1-heptyl, and 1-octyl. The term "$(C_1-C_3)$alkyl-O—" means the $(C_1-C_3)$alkyl bonded to an oxygen atom radical.

The term "captive polymerization inhibitor" means a substance that does not evaporate and condense in the second polymerization inhibiting amount with the acrylic acid-type monomer of formula (M) in the condensate mixture produced by the method of the second embodiment.

The terms "chloro" and "fluoro" respectively mean a radical of a chlorine atom or fluorine atom.

The term "condensate" means a liquid phase formed from a substance in a gaseous or vaporous phase.

The term "distillable monomer" means a compound that is capable of being evaporated from the first location and condensed (i.e., returned to a liquid form) at the second location, preferably producing a condensate mixture at the second location having at least 50 wt % recovered of an initial amount of the compound at the first location and more preferably also in a compound purity at the second location greater than compound purity at the first location. Examples of distillable monomers are olefinic monomers and free-radical polymerizable monomers. The term "olefinic monomer" means a compound having a carbon-carbon double bond or carbon-carbon triple bond and being distillable in the method of the second embodiment. Preferably the distillable monomer has a boiling point of 250 degrees Celsius or less at an absolute pressure of 1 atmosphere (101 kiloPascals) or less. An example of the olefinic monomer is a vinyl monomer. The vinyl functional group of the vinyl monomer is substituted (e.g., has a moiety $(C_1-C_3)$alkyl)-C(H)=C(H)—) or unsubstituted (i.e., has a moiety $H_2C=C(H)$—).

The term "evaporated" means converted from a liquid phase to a gaseous phase. Examples of evaporation include conversions at ambient temperature (e.g., 25 degrees Celsius (° C.)) and pressure (e.g., 101 kiloPascals (kPa)) and conversions at higher than ambient temperature, pressure, or both.

The term "fugitive polymerization inhibitor" means a substance that is capable of evaporating and condensing in the second polymerization inhibiting amount with the distillable monomer (e.g., acrylic acid-type monomer of formula (M)) in the condensate mixture produced by the method of the second embodiment. In the invention process, the second polymerization inhibiting amount of the fugitive polymerization inhibitor is derived from the first polymerization inhibiting amount thereof.

The term "inhibit" means to delay onset of, reduce degree of, or, preferably, prevent that which is being inhibited.

The phrase "inhibitor of polymerization of at least one acrylic acid-type monomer of formula (M)" means a compound, or a combination of the compound and an inhibitor modifier, that prevents visual appearance of solid poly (acrylic acid-type monomer of formula (M)) for an average time value of at least 30 hours. The term "inhibitor modifier" means a substance (e.g., the manganese salt) that generates or regenerates the compound from a derivative thereof. The time is determined using the following procedure: seal a glass vial containing a liquid mixture of the acrylic acid-type monomer of formula (M) and 100 ppm of the compound or 100 ppm of the compound and 20 ppm of the inhibitor modifier, based on total weight of the liquid mixture. Place the vial in a mineral oil bath thermostated at 113° C. Record time to the visual appearance of solid poly(acrylic acid-type monomer of formula (M)) anywhere in the vial (i.e., in the liquid mixture or on wall of vial above the liquid mixture). Repeat 4 times. Average the five times to give the average time value.

The term "nitroso" means a compound having a structural fragment of formula

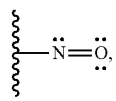

wherein

means a portion of a covalent bond. The term "nitroxide" means a compound having a structural fragment of formula

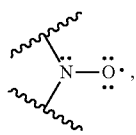

wherein each

means a portion of a covalent bond. In phenylnitroxide, for example, a $C_6H_5$— (phenyl) and hydrogen are bonded to the nitrogen to give

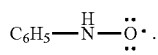

The phrase "not interconvertible between one another" means one substance would not convert in situ to another substance, or vice versa, during a course of inhibiting polymerization of the distillable monomer according to the method of the second embodiment. Thus, for example, the composition of the first embodiment contemplates a mixture of the fugitive polymerization inhibitor that is nitrosobenzene and the captive polymerization inhibitor that is 2-chlorophenylnitroxide, but not a mixture of nitrosobenzene and phenylnitroxide. Preferably, the captive polymerization inhibitor is not a nitroxide compound.

The term "polymerization inhibiting amount" means an absolute weight (e.g., in grams) or relative weight (e.g., expressed in parts per million (ppm) or weight percent (wt %)) of a substance that is sufficient to delay onset of, reduce degree of, or, preferably, prevent polymerization. The term "sufficient to" means "effective for," e.g., effective for delaying onset of, reducing degree of, or, preferably, preventing polymerization. For example, 1 ppm equals 1 milligram per 1000 grams (or 1 gram per 1000 kilograms, and the like) or 0.0001 wt %.

The phrase "polymerization is inhibited" and the like means where a polymerizable monomer is exposed to polymerization conditions (a chemical process resulting in bonding between two or more molecules of the polymerizable monomer to produce an organic oligomer or polymer thereof) and the polymerizable monomer is in contact with the captive polymerization inhibitor, the fugitive polymerization inhibitor, or both, rate of the chemical process is lowered compared to a rate of the chemical process in absence of such inhibitor(s).

Fugitive Polymerization Inhibitors

The fugitive polymerization inhibitor is especially useful for inhibiting polymerization of the distillable monomer at a second location where condensation of the fugitive polymerization inhibitor and the distillable monomer can occur such as, for example, in a distillation column, headspace, or a trapped gas location that is in fluid communication with the distillation vessel, storage vessel, or conduit, respectively. Preferably the second location is distal from (i.e., not in range of direct liquid communication with (e.g., not in splashable contact with, and preferably including a site furthest away from) the first location.

It is not critical which fugitive polymerization inhibitor is used. The fugitive polymerization inhibitors do not include derivatives of the distillable monomer (e.g., acrylic acid-type monomer of formula (M)). Preferably, the fugitive polymerization inhibitor is an inhibitor of the acrylic acid-type monomer of formula (M), more preferably a nitroso compound of formula (I):

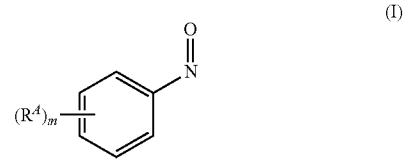

wherein m is an integer of from 1 to 3 and each $R^A$ independently is hydrogen, $(C_1-C_3)$alkyl, $(C_1-C_3)$alkyl-O—, fluoro, or chloro. Preferred is the nitroso compound of formula (I) wherein m is 2 or 3 and each $R^A$ independently is $(C_1-C_3)$alkyl, $(C_1-C_3)$alkyl-O—, fluoro, or chloro. More preferred is the nitroso compound of formula (I) wherein m is 1 and $R^A$ is $(C_1-C_3)$alkyl, $(C_1-C_3)$alkyl-O—, fluoro, or chloro. Still more preferred is the nitroso compound of formula (I) m is 1 and $R^A$ is hydrogen. The present invention further contemplates employing a combination of any two or more of the aforementioned fugitive polymerization inhibitors.

A polymerization inhibiting amount of the nitroso compound of formula (I) can be varied depending on, for example, the particular acrylic acid-type monomer and amount thereof being inhibited, conditions such as temperature and pressure, presence or absence of other polymerization inhibitors, and vapor pressure of the nitroso compound of formula (I). An invention process may be initiated with a larger polymerization inhibiting amount than is believed required. Thereafter the polymerization inhibiting amount can be allowed to decrease (e.g., as polymerization inhibitor is reacted) until a desirable steady-state amount of polymerization inhibitor is obtained under the conditions (e.g., as evidenced by achieving a desired time interval between column cleanings). A person of ordinary skill in the art would be able to determine appropriate polymerization inhibiting amounts under particular circumstances without undue experimentation. A preferred first polymerization inhibiting amount of the nitroso compound of formula (I) is from greater than 25 ppm to about 2000 ppm, more preferably greater than 50 ppm, still more preferably greater than 75 ppm, and even more preferably greater than 100 ppm; and more preferably about 1000 ppm or less, still more preferably about 500 ppm or less, and even more preferably about 200 ppm or less, all based on a total weight of the liquid mixture. A preferred second polymerization inhibiting amount of the evaporated and condensed nitroso compound of formula (I) is from about 25 ppm to less than 2000 ppm, more preferably at least about 50 ppm, still more preferably at least about 75 ppm, and even more preferably at least about 100 ppm; and more preferably less than 1000 ppm, still more preferably less than 500 ppm, and even more preferably less than 200 ppm, all based on a total weight of the condensate mixture.

Syntheses of nitrosobenzene are known and are readily adapted for synthesis of the compound of formula (I). Some syntheses reduce nitrobenzene to give nitrosobenzene, whereas other syntheses oxidize phenylhydroxylamine. See, for example, (a) *Organic Synthesis*, Collective Volume 3, 1955, page 668; (b) ibid, Volume 25, 1945, page 80; and Favre T L F, et al., Catalyst Letters 1, 1988, 457-460.

Synthesis of the nitroso compound of formula (I) is not critical to the invention and all successful syntheses are contemplated. In some embodiments, the nitroso compound of formula (I) is synthesized by reducing a corresponding nitro compound of formula (IA) as shown below in Scheme 1.

Scheme 1.

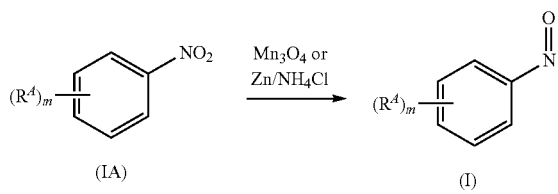

wherein m and $R^A$ are as described for the first embodiment. In Scheme 1, a nitrobenzene compound of formula (IA) is contacted with a selective 2-electron reducing compound such as, for example, unpromoted $Mn_3O_4$ or a mixture of zinc (Zn) and ammonium chloride ($NH_4Cl$) in a suitable solvent (e.g., water) at a selective reducing temperature, preferably from about 0° C. to about 100° C., to give the nitroso compound of formula (I). The procedure outlined in Scheme 1 is preferred when each $R^A$ independently is hydrogen, $(C_1-C_3)$alkyl, or $(C_1-C_3)$alkyl-O—.

In some embodiments, the nitroso compound of formula (I) is synthesized by oxidizing a corresponding hydroxylamino compound of formula (IB) as shown below in Scheme 2.

Scheme 2.

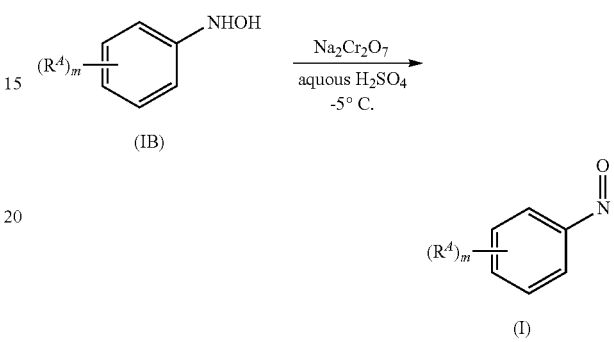

wherein m and $R^A$ are as described for the first embodiment. In Scheme 2, a hydroxylamine compound of formula (IB) is contacted with a selective 2-electron oxidizing compound such as, for example, sodium dichromate dihydrate ($Na_2Cr_2O_7.2H_2O$), in a suitable solvent (e.g., water) at a selective reducing temperature, preferably from about 0 degrees Celsius (° C.) to about 100° C., to give the nitroso compound of formula (I). The procedure outlined in Scheme 2 is preferred when each $R^A$ independently is hydrogen, $(C_1-C_3)$alkyl-O—, fluoro, or chloro.

Captive Polymerization Inhibitors

The captive polymerization inhibitor (and also the fugitive polymerization inhibitor) is especially useful for inhibiting polymerization of the distillable monomer at a first location such as in a distillation vessel (pot), storage vessel, or conduit (piping).

It is not critical which captive polymerization inhibitor is used. The captive polymerization inhibitors do not include derivatives of the distillable monomer (e.g., acrylic acid-type monomer of formula (M)). In some embodiments, the captive polymerization inhibitor is an inhibitor of the acrylic acid-type monomer of formula (M), more preferably a manganese salt that is $Mn(HCO_2^-)_2$, $Mn((C_1-C_8)alkyl CO_2^-)_2$, or potassium permanganate. In some embodiments, the manganese salt is employed in a method of the second embodiment as the inhibitor modifier in combination with the captive polymerization inhibitor. A preferred polymerization inhibiting amount of the compound of formula (II) is from about 5 ppm to about 500 ppm, more preferably from about 10 ppm to about 250 ppm, still more preferably from about 20 ppm to about 200 ppm, and even more preferably from about 40 ppm to about 100 ppm, all based on a total weight of the liquid mixture.

In some embodiments, the manganese salt is $Mn(HCO_2^-)_2$. In some embodiments, the manganese salt is $Mn((C_1-C_8)alkylCO_2^-)_2$, and more preferably manganese (II) acetate, including manganese(II) acetate ($Mn(O_2CCH_3)_2$) and manganese(II) acetate tetrahydrate ($Mn(O_2CCH_3)_2.4H_2O$). In some embodiments, the manganese salt is potassium permanganate.

In some embodiments, the captive polymerization inhibitor is hydroquinone.

In some embodiments, the captive polymerization inhibitor is phenothiazine. The term "phenothiazine" means the compound of the following formula:

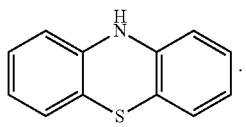

A polymerization inhibiting amount of the manganese salt, hydroquinone, or phenothiazine can vary depending on, for example, the particular acrylic acid-type monomer and amount thereof being inhibited, conditions such as temperature and pressure, presence or absence of other polymerization inhibitors, and amount of inhibitor modifier, if any, that is present. The person of ordinary skill in the art would be able to determine appropriate polymerization inhibiting amounts under particular circumstances without undue experimentation. A preferred polymerization inhibiting amount of the manganese salt, hydroquinone, or phenothiazine independently is from about 5 ppm to about 500 ppm, more preferably from about 10 ppm to about 250 ppm, still more preferably from about 20 ppm to about 200 ppm, and even more preferably from about 40 ppm to about 100 ppm, all based on a total weight of the liquid mixture.

In some embodiments, the captive polymerization inhibitor is a compound of formula (II):

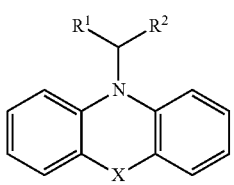

(II)

or a second acid addition salt thereof, wherein X is S, O, or N—$R^3$; $R^1$ is hydrogen or $(C_1$-$C_3)$alkyl; $R^2$ is phenyl; and $R^3$ is $(C_1$-$C_3)$alkyl. In some embodiments, the compound of formula (II) is one wherein X is S. In some embodiments, X is O. In some embodiments, X is N—$R^3$. Preferably, $R^3$ is methyl.

In some embodiments, the compound of formula (II) is one wherein $R^1$ is hydrogen. In some embodiments, $R^1$ is $(C_1$-$C_3)$alkyl, and more preferably, $R^1$ is methyl.

In some embodiments, the captive polymerization inhibitor comprises a combination of hydroquinone and either phenothiazine or the compound of formula (II).

A polymerization inhibiting amount of the compound of formula (II) can vary depending on, for example, the particular acrylic acid-type monomer and amount thereof being inhibited, conditions such as temperature and pressure, presence or absence of other polymerization inhibitors, and amount of inhibitor modifier, if any, that is present. The person of ordinary skill in the art would be able to determine appropriate polymerization inhibiting amounts under particular circumstances without undue experimentation. A preferred polymerization inhibiting amount of the compound of formula (II) is from about 5 ppm to about 500 ppm, more preferably from about 10 ppm to about 250 ppm, still more preferably from about 20 ppm to about 200 ppm, and even more preferably from about 40 ppm to about 100 ppm, all based on a total weight of the liquid mixture.

Synthesis of the compound of formula (II) is not critical to the invention and all successful syntheses are contemplated. In some embodiments, the compound of formula (II) is synthesized by alkylating a corresponding intermediate amino compound of formula (IIA) as shown below in Scheme 3.

Scheme 3.

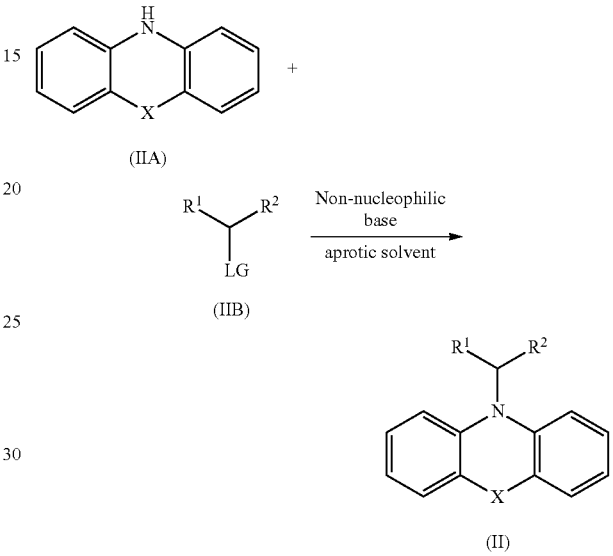

wherein X, $R^1$, and $R^2$ are as described for the first embodiment and LG is a leaving group. In Scheme 3, an amino compound of formula (IIA) and a compound of formula (IIB) having a leaving group are contacted in the presence of a non-nucleophilic strong base and aprotic solvent at a nucleophilic displacement temperature, preferably from about 0° C. to about 100° C., to give the compound of formula (II). Examples of aprotic solvents are tetrahydrofuran, 1,2-dimethoxyethane, and dioxane. Examples of the non-nucleophilic base are sodium hydride, potassium hydride, potassium hexamethyldisilazide (KHMDS), and lithium diisopropylamide (LDA). Examples of leaving groups are iodo, bromo, chloro, an activated hydroxyl, trifluoromethanesulfonate, trifluoroacetate, and tosylate. In some embodiments, such activated hydroxyls are prepared from a compound of formula (IIB) wherein LG is HO— and a coupling agent such as, for example, triphenylphosphine with either diisopropylazodicarboxylate (DIAD), 1-(3-dimethylaminopropyl)-3-ethylcarbodiimide hydrochloride (EDC, EDCI, or EDAC), N,N'-carbonyldiimidazole (CDI), or N,N'-dicyclohexylcarbodiimide (DCC), and optionally with 1-hydroxybenzotriazole (HOBt); and (benzotriazol-1-yloxy)tripyrrolidino-phosphonium hexafluorophosphate.

Other syntheses of the compound of formula (II) are contemplated. For example when $R^1$ is hydrogen, the compound of formula (II) can be synthesized by coupling the compound of formula (IIA) with an acid halide of formula halo-C(=O)—$R^2$ or acid anhydride of formula $R^2$—C(=O)—O—C(=O)—$R^2$ to give a penultimate carboxamide of formula (IIC):

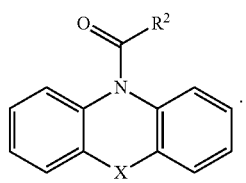

(IIC)

The carboxamide of formula (IIC) can then be reduced (e.g., lithium aluminum hydride in tetrahydrofuran) to give the compound of formula (II).

The invention further contemplates employing acid addition salts of the compound of formula (II). The term "acid addition salt" means an ionic substance comprising an organic cation and an organic, or preferably inorganic anion. The organic cation comprises a protonated form of phenothiazine or the compound of formula (II). The anion comprises a residual of an organic or, preferably, inorganic compound having at least one proton characterized by a pKa value of less than 7 (i.e., a residual of a Brønsted acid). Preferred acid addition salts comprise from 0.9 to 1.1 mole equivalents of a monoprotic Brønsted acid, from 0.45 to 0.55 mole equivalents of a diprotic Brønsted acid, or from 0.3 to 0.37 mole equivalents of a triprotic Brønsted acid, all per mole of phenothiazine or the compound of formula (II). Preferred Brønsted acids include hydrochloric, nitric, phosphoric, sulfuric, hydrobromic, hydroiodic, phosphorus, formic, and acetic acids.

In some embodiments, the captive polymerization inhibitor comprises a first mixture of an N-oxyl compound and the manganese salt that is $Mn(HCO_2^-)_2$, $Mn((C_1-C_8)alkyl\ CO_2^-)_2$, or potassium permanganate. The term "N-oxyl compound" means a chemical substance having a structural fragment,

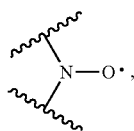

wherein the . represents a radical (electron) and each

represents a portion of a covalent bond to a quaternary carbon atom. Preferably, the N-oxyl compound is 2,2,5,5-tetramethyl-3-oxopyrrolidine-1-oxyl; 2,2,6,6-tetramethylpiperidine-1-oxyl; tris(2,2,6,6-tetramethylpiperidine-1-oxyl-4-yl)-phosphite; and, more preferably, 4-hydroxy-2,2,6,6-tetramethylpiperidine-1-oxyl. The terms "4-hydroxy-2,2,6,6-tetramethylpiperidine-1-oxyl" and "4-hydroxy-TEMPO" are synonymous and each mean a compound of the following formula:

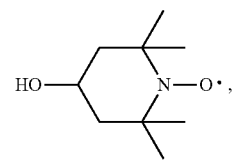

wherein the . represents a radical (electron).

The present invention further contemplates employing a combination of any two or more of the aforementioned captive polymerization inhibitors.

A polymerization inhibiting amount of 4-hydroxy-TEMPO can vary depending on, for example, the particular acrylic acid-type monomer and amount thereof being inhibited, conditions such as temperature and pressure, presence or absence of other polymerization inhibitors, and amount of the manganese salt present. The person of ordinary skill in the art would be able to determine appropriate polymerization inhibiting amounts under particular circumstances without undue experimentation. A preferred polymerization inhibiting amount of the N-oxyl compound such as 4-hydroxy-TEMPO is from about 5 ppm to about 500 ppm, more preferably from about 10 ppm to about 250 ppm, still more preferably from about 20 ppm to about 200 ppm, and even more preferably from about 40 ppm to about 100 ppm, all based on a total weight of the liquid mixture.

A preferred acrylic acid-type monomer polymerization inhibitor composition is one wherein any one of the preferred nitroso compounds of formula (I) is combined with any one of the preferred captive polymerization inhibitors described herein.

Inhibitor Modifier

Examples of the inhibitor modifier are molecular oxygen (e.g., when the captive polymerization inhibitor is phenothiazine or the compound of formula (II)) and the manganese salt (e.g., when the captive polymerization inhibitor is the N-oxyl compound (e.g., the 4-hydroxy-2,2,6,6-tetramethylpiperidine-1-oxyl) or the compound of formula (II)).

Acrylic Acid-Type Monomers of Formula (M)

Preferred is the acrylic acid-type monomer of formula (M) wherein one of $R^{11}$ to $R^{14}$ is $(C_1-C_8)$alkyl and the remainder of $R^{11}$ to $R^{14}$ is hydrogen. In some embodiments, $R^{11}$ is $(C_1-C_{18})$alkyl. In some embodiments, $R^{11}$ is $(C_9-C_{18})$alkyl. In some embodiments, $R^{11}$ is $(C_1-C_8)$alkyl. In some embodiments, $R^{11}$ is $(C_1-C_8)$alkyl and each of $R^{12}$ to $R^{14}$ is hydrogen. In some embodiments, $R^{12}$ is $(C_1-C_8)$alkyl and each of $R^{11}$, $R^{13}$, and $R^{14}$ is hydrogen. In some embodiments, $R^{13}$ is $(C_1-C_8)$alkyl and each of $R^{11}$, $R^{12}$, and $R^{14}$ is hydrogen. In some embodiments, $R^{14}$ is $(C_1-C_8)$alkyl and each of $R^{11}$ to $R^{13}$ is hydrogen. In some embodiments, each of $R^{11}$ to $R^{14}$ is hydrogen, i.e., the acrylic acid-type monomer of formula (M) is acrylic acid itself.

Also preferred is the acrylic acid-type monomer of formula (M) wherein two of $R^{11}$ to $R^{14}$ is $(C_1-C_8)$alkyl and the remainder of $R^{11}$ to $R^{14}$ is hydrogen. More preferably, $R^{11}$ is one of the two of $R^{11}$ to $R^{14}$ that is $(C_1-C_8)$alkyl.

Also preferred is the acrylic acid-type monomer of formula (M) wherein three of $R^{11}$ to $R^{14}$ is $(C_1-C_8)$alkyl and the remainder of $R^{11}$ to $R^{14}$ is hydrogen.

Preferably in the acrylic acid-type monomer of formula (M), each $(C_1-C_8)$alkyl is $(C_1-C_3)$alkyl and, more preferably, methyl.

Compounds of formulas (I), (II), and (M), 4-hydroxy-TEMPO, manganese salts, acid addition salts, inhibitor modifier, etc. useful in the present invention include solvates, including hydrates, thereof.

Preferably in the composition of the first embodiment, the distillable monomer (e.g., acrylic acid-type monomer of formula (M)) and the fugitive polymerization inhibitor are distillation compatible, distillation performance matched to each other in order to establish a means for better co-evaporation and co-condensation thereof during a method of the second embodiment. Thus, such performance matching provides better inhibition of polymerization of the latter by the former at, for example, distal structures during distillation than inhibition provided by randomly matched distillable monomer and the fugitive polymerization inhibitor. More preferably, the performance matching includes some embodiments of the composition of the first embodiment wherein the distillable monomer (e.g., acrylic acid-type monomer of formula (M)) and the fugitive polymerization inhibitor are characterized by either (i) respective first and second liquid vapor pressures of substantially pure forms thereof or (ii) relative volatility of a test mixture consisting essentially of the distillable monomer, the fugitive polymerization inhibitor, and the captive polymerization inhibitor, wherein the first and second liquid vapor pressures are independently determined at a same elevated temperature, the elevated temperature being 50 degrees Celsius or higher, and the first liquid vapor pressure and the second liquid vapor pressure independently are at least 5 kiloPascals (in some embodiments at least 10 kiloPascals and in some embodiments at least 10 kiloPascals and less than 200 kiloPascals) and are within 40 kiloPascals of each other; and the relative volatility of the test mixture is from 0.5 to 10. Preferably, the first and second liquid vapor pressures are within about 30 kPa, more preferably within about 20 kPa, and still more preferably within about 10 kPa of each other at the elevated temperature of the liquid mixture. Preferably, the relative volatility is 5 or less, and more preferably 2 or less.

The term "relative volatility" means a ratio ($\alpha_{i,m}$) of distribution coefficients, the ratio equal to (vapor phase mole fraction ($y_i$) divided by liquid phase mole fraction ($x_i$) for the fugitive polymerization inhibitor) divided by (vapor phase mole fraction ($y_m$) divided by liquid phase mole fraction ($x_m$) for the distillable monomer (e.g., acrylic acid-type monomer of formula (M))). That is, relative volatility=$\alpha_{i,m}$=$(y_i/x_i)/(y_m/x_m)$. Relative volatility is determined by conventional methods such as, for example, those methods described in Chapters 1 to 4 of Robinson C S and Gilliland E R, *Elements of Fractional Distillation*, 4$^{th}$ edition, 1950, McGraw-Hill Book Company, New York, N.Y., USA.

The term "substantially pure" means a purity as determined by gas chromatography of 95.1 weight percent (wt %) or higher, preferably 97.1 wt % or higher, more preferably 98.1 wt % or higher, and still more preferably 99.1 wt % or higher. The phrase "test mixture consisting essentially of" means a material for determining relative volatilities, the material being formed by intimately contacting together substantially pure forms of components that are recited immediately following the phrase.

In some embodiments, the characterization of the distillable monomer (e.g., acrylic acid-type monomer of formula (M)) and the fugitive polymerization inhibitor comprises the first and second liquid vapor pressures of the substantially pure forms thereof. In some embodiments, the characterization the distillable monomer and the fugitive polymerization inhibitor comprises the relative volatility of the test mixture. More preferably, the characterization of the distillable monomer and the fugitive polymerization inhibitor is the one that would provide a higher second polymerization inhibiting amount of the evaporated and condensed fugitive polymerization inhibitor during the method of the second embodiment.

Inhibiting Polymerization of Distillable Monomers (e.g., Acrylic Acid-Type Monomers)

In the method of the second embodiment the distillable monomer is exposed to polymerizing conditions and thus susceptible to being polymerized (e.g., susceptible to forming an oligomer or homopolymer), and any polymerization of the distillable monomer in the invention method is inhibited by the fugitive and captive polymerization inhibitors. Examples of polymerizing conditions are exposure to a polymerizing agent (e.g., oxygen gas, water, or a free radical or initiator) or condition (e.g., free radical generation conditions such as ultraviolet light or a high temperature zone).

The evaporating and condensing steps of the method of the second embodiment can be repeated numerous times (as in a conventional purification by distillation) before the condensate mixture is formed at the second location. Each such repetition would thereby form intermediate condensate mixtures at locations intermediate between the first and second locations. As mentioned previously, the condensate mixture at the second location contains a polymerization inhibiting amount of the fugitive inhibitor (i.e., the second polymerization inhibiting amount thereof), and preferably most, and more preferably each of the intermediate condensate mixtures formed between the first and second locations also independently contain a polymerization inhibiting amount of the fugitive inhibitor, any two of such amounts being the same or different.

The captive polymerization inhibitors preferably also inhibit in situ conversion (e.g., conversion in a distillation pot) of the fugitive polymerization inhibitors to other captive polymerization inhibitors, and thus allow condensing at the second location (e.g., distal structures) the second polymerization inhibiting amounts of the evaporated fugitive polymerization inhibitors as described in the second embodiment.

A preferred method of the second embodiment employs any one of the preferred acrylic acid-type monomer polymerization inhibitor compositions described herein and any one of the preferred acrylic acid-type monomers of formula (M) described herein. Another preferred of the second embodiment employs a mixture of any two or more of the preferred acrylic acid-type monomers of formula (M) described herein such as, for example, a mixture of acrylic acid and either ethyl acrylate or n-butyl acrylate.

Preferably in the method of the second embodiment employing the acrylic acid-type monomer of formula (M) and captive and fugitive polymerization inhibitors thereof, the step (b) comprises evaporating at least some of the acrylic acid-type monomer of formula (M) and at least some of the fugitive polymerization inhibitor under a reduced pressure that is less than 90 kPa and an elevated temperature of the liquid mixture (e.g., distillation pot temperature) that is greater than 50° C., and more preferably greater than 90° C. More preferably, in the step (b), the acrylic acid-type monomer of formula (M) is characterized by a first liquid vapor pressure and the fugitive polymerization inhibitor is characterized by a second liquid vapor pressure, and the first liquid vapor pressure and the second liquid vapor pressure independently are at least 10 kiloPascals and are within about 40 kPa of each other at the elevated temperature of the liquid mixture. Preferably, the first and second liquid vapor pressures are within about 30 kPa, more preferably within about 20 kPa, and still more preferably within about 10 kPa of each other at the elevated temperature of the liquid mixture.

The person of ordinary skill in the art would be able to determine appropriate elevated temperatures of the liquid mixtures containing distillable monomers under particular circumstances without undue experimentation. For example, separately obtain from published literature or, if necessary, measure vapor pressures at progressively higher measurement temperatures for the nitroso compound of formula (I) and the acrylic acid-type monomer of formula (M) by conventional means. Then compare the liquid vapor pressures of the nitroso compound of formula (I) and the acrylic acid-type monomer of formula (M) at same measurement temperatures to identify the appropriate elevated temperatures of the liquid mixtures comprising same and the captive polymerization inhibitor. Assume the captive polymerization inhibitor does not materially affect the liquid vapor pressures. Preferably, graphically plot the liquid vapor pressures versus the measurement temperatures, and identify the appropriate elevated temperatures of the liquid mixtures from the plots. By way of illustration, liquid vapor pressures of substantially pure forms of nitrosobenzene, acrylic acid, and n-butyl acrylate (i.e., $H_2C=C(H)CO_2(CH_2)_3CH_3$) at various measurement temperatures are respectively shown below in Table A.

TABLE A measurement temperature versus liquid vapor pressure data for nitrosobenzene, acrylic acid, and n-butyl acrylate

| Measurement Temperature (° C.) | Nitrosobenzene Substantially Pure Liquid Vapor Pressure (kPa) | Acrylic Acid Substantially Pure Liquid Vapor Pressure (kPa) | n-butyl acrylate Substantially Pure Liquid Vapor Pressure (kPa) |
|---|---|---|---|
| 60 | N/a* | 3.76 | 4.25 |
| 70 | 6.88 | 6.26 | 6.79 |
| 80 | 10.39 | 10.06 | 10.50 |
| 90 | 14.91 | 15.65 | 15.77 |
| 100 | 20.87 | 23.66 | 23.05 |
| 110 | 28.70 | 34.86 | 32.88 |
| 120 | 38.84 | 50.15 | 45.87 |
| 130 | 51.72 | 70.59 | 62.71 |
| 140 | 67.77 | 97.43 | 84.16 |
| 150 | 87.42 | 132.06 | 111.05 |
| 160 | 111.11 | 176.03 | 144.27 |

*Not applicable; nitrosobenzene is a solid at 60° C.

The data in Table A are graphically plotted in FIG. 1. In FIG. 1 and Table A, a particularly useful elevated temperature range for the method of the second embodiment employing the acrylic acid-type monomer of formula (M) and the captive and fugitive polymerization inhibitors thereof is shown to be from about 70° C. to about 140° C. In some embodiments the elevated temperature range of from about 100° C. to about 120° C. is an appropriate elevated temperature for the respective liquid mixtures comprising nitrosobenzene, acrylic acid or n-butyl acrylate, and the captive polymerization inhibitor. The elevated temperature range of from about 100° C. to about 120° C. is more preferred for each of the liquid mixtures, especially in a manufacturing reduced-pressure distillation operation. The more preferred elevated temperature range allows a slower rate of polymerization of the acrylic acid or n-butyl acrylate monomer than does 150° C. or 160° C., while still allowing evaporation and condensation of sufficient polymerization inhibiting amounts of nitrosobenzene together with evaporated and condensed monomers. The elevated temperature range of about 100° C. is also preferred for the liquid mixture comprising nitrosobenzene, ethyl acrylate, and the captive polymerization inhibitor.

In a pilot plant or manufacturing setting, a preferred distillation column is one that contains dual-flow plates or trays. An example of such a dual-flow tray column is described in U.S. Pat. No. 7,306,204 B2. Preferably, distillation columns comprise, and the liquid mixture is in sequential fluid communication with, bottom, middle and upper zones, wherein the middle zone optionally defines a feed inlet. In a method of the second embodiment, preferably during steady state operation temperature in the bottom zone is within about 5° C. of the elevated temperature of the liquid mixture and reduced pressure in the top zone is within about 30 kPa of reduced pressure in the bottom zone. For illustration, a manufacturing scale dual-flow 40-tray column during steady state operation is characterized by a temperature of about 111° C. and reduced pressure of about 35 kPa in its bottom zone, a temperature of about 46° C. and reduced pressure of about 21 kPa in its top zone, and a temperature of about 56° C. in its middle zone.

The present invention contemplates batch (single addition of distillable monomer) and continuous (continuous addition or multiple separate additions of distillable monomer) processes of the second embodiment. In batch or continuous processes, especially continuous processes, preferably one or more additional polymerization inhibiting amounts of the captive polymerization inhibitor, fugitive polymerization inhibitor, or both are added to the distillable monomer. For example in a continuous process employing a distillation vessel (e.g., distillation pot) and column, such one or more additional polymerization inhibiting amounts can be added to the distillation vessel containing distillable monomer so as to replace amounts of the captive polymerization inhibitor lost to reaction thereof in the distillation vessel, amounts of the fugitive polymerization inhibitor lost to reaction thereof in the distillation vessel or distillation column or lost via distillation away from the distillation column (e.g., to a distillate receiving vessel for receiving distilled monomer and fugitive polymerization inhibitor). The additions of polymerization inhibitor independently comprise continuous or multiple separate additions and can be made by conventional means such as, for example, an addition funnel or valved feed line. For example, an addition of an amount of the fugitive polymerization inhibitor to the first location can be made at a sufficient rate, and if necessary the rate of addition can be adjusted periodically, so as to maintain a desired second polymerization inhibiting amount of fugitive polymerization inhibitor at the second location.

PREPARATION(S) AND GENERAL METHOD(S)

Acrylic acid, nitrosobenzene, phenothiazine, 4-hydroxy-TEMPO and a number of manganese salts are commercially available from various suppliers including Sigma-Aldrich Company, St. Louis, Mo., USA.

Preparation 1: synthesis of N-benzylphenothiazine (1)

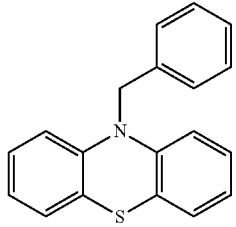

Add a solution of 2 grams (g; 0.01 mole (mol)) of phenothiazine in 10 milliliters (mL) of dry tetrahydrofuran (THF) under nitrogen gas atmosphere to a suspension of 1.0 g of sodium hydride (NaH; 0.042 mol) in 20 mL of dry THF at room temperature (Previously obtain the NaH by washing an 80% suspension of NaH in mineral oil with n-hexane.) Stir the mixture for 4 hours or until hydrogen gas is released and the color of mixture changes to orange. Then slowly add 2 mL (0.017 mol) of benzyl bromide to the orange mixture at room temperature, and stir the resulting mixture overnight. Heat the mixture to 60° C. for 1 hour. The orange color fades. Pour the reaction mixture into ice-water that has been acidified with concentrated hydrochloric acid to pH 1. Extract the resulting aqueous mixture with ethyl acetate, dry it over anhydrous magnesium sulfate, and remove the solvent under vacuum. Purify the resulting extraction residue by column chromatography over neutral alumina eluting with a solvent mixture of n-hexane:ethyl acetate (50:1). Evaporate the solvents and recrystallized the residue from ethanol to give 2 g (60% yield) of N-benzylphenothiazine as white crystals. $^1$H NMR spectrum is consistent with pure N-benzylphenothiazine. $^1$H NMR (CDCl$_3$) (ppm): 7.25-7.40 (m, 5H); 7.11 (d, 2H, J=7.5 Hz); 7.00 (t, 2H, J=8.0 Hz); 6.88 (t, 2H, J=7.5 Hz); 6.67 (d, 2H, J=8.0 Hz); 5.12 (s, 2H).

Preparation 2: synthesis of
N-(1-phenylethyl)-phenothiazine (2)

(2)

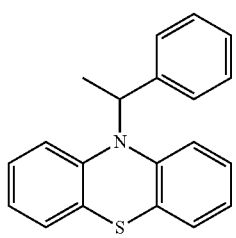

In a procedure similar to that of Preparation 1 except use (1-bromoethyl)benzene instead of benzyl bromide, prepare N-(1-phenylethyl)-phenothiazine. Product is purified by column chromatography on neutral alumina using n-hexane: ethyl acetate (50:1) mixture of solvents as an eluent. Evaporation of solvent gave N-(1-phenylethyl)-phenothiazine as a white solid in 65% yield. $^1$H NMR spectrum is consistent with N-(1-phenylethyl)-phenothiazine. $^1$H NMR (CDCl$_3$) (ppm): 7.30-7.45 (m, 5H, Ar—CH—); 7.14 (d, 2H, J=7.5 Hz, Ar—PTZ); 6.85-7.05 (m, 4H, Ar—PTZ); 6.74 (d, 2H, J=7.0 Hz, Ar—PTZ); 5.42 (q, 1H, Ar—CH—CH$_3$); 1.98 (d, 3H, J=7.0 Hz, CH—CH$_3$).

EXAMPLES OF THE PRESENT INVENTION

Initial attempts to discover a fugitive inhibitor having distillation performance compatible with distillation performance of a divinylbenzene have been unsuccessful as of the instant filing date.

Examples 1 to 5

Mixtures of Nitrosobenzene and Captive Polymerization Inhibitors

Mix nitrosobenzene and a captive polymerization inhibitor in the amounts expressed in milligrams (mg) listed in Table 1 to give mixtures of Examples 1 to 5. The mixtures of Examples 1 to 5 are particularly useful for inhibiting polymerization of acrylic acid (e.g., 7 g of acrylic acid).

TABLE 1 mixtures of nitrosobenzene and captive polymerization inhibitors

| Example Number | Mixtures of nitrosobenzene and captive polymerization inhibitors |
|---|---|
| 1 | 0.7 mg nitrosobenzene, 0.7 mg 4-hydroxy-TEMPO, and 0.07 mg of manganese acetate tetrahydrate |
| 2 | 0.7 mg nitrosobenzene, 0.7 mg N-benzylphenothiazine, and air |
| 3 | 0.7 mg nitrosobenzene, 0.7 mg N-(1-phenylethyl)-phenothiazine, and air |
| 4 | 1.4 mg nitrosobenzene and 0.07 mg of manganese acetate tetrahydrate |
| 5 | 3.5 mg nitrosobenzene and 0.07 mg of manganese acetate tetrahydrate |

Example 6

Mix 0.7 mg nitrosobenzene, 0.7 mg phenothiazine, and air.

Examples 7 to 12

Inhibition of Polymerization of Evaporated and Condensed Acrylic Acid Monomer

General procedure: assembly a system comprising a Schlenk flask equipped with a magnetic stir bar and a packed column. In separate experiments, charge the Schlenk flask with 7 g acrylic acid and a mixture of any one of Examples 1 to 6, respectively, to give an acrylic acid-inhibitor mixture. Place the flask in an oil bath thermostated at 113° C. and stir the mixtures with a magnetic stirrer. Decrease pressure in the flask to either 110 millibars (11 kPa) or 85 millibars (8.5 kPa), and reflux the acrylic acid-inhibitor mixture until, and record time of reflux to, the visual appearance of solid poly(acrylic acid) anywhere in the system. Results are shown later in Table 2.

For comparison, repeat procedure of Example 13a except use 4-nitrosophenol instead of nitrosobenzene. Results are also shown in Table 2.

TABLE 2 reflux time to visual appearance of solid poly(acrylic acid)

| Example Number | Example Number of mixture tested | reflux time to visual appearance of solid poly(acrylic acid) (hours) |
|---|---|---|
| None (comparative) | None (comparative) | 1** |
| 7 | 1 | 14 |
| 8 | 2 | Not determined |
| 9 | 3 | Not determined |
| 10 | 4 | 11(110 mbar); 21(85 mbar) |
| 11 | 5 | 20 |
| 12 | 6 | 6*** |

**result with 4-nitrosophenol instead of nitrosobenzene;
***use 3.5 milligrams each of nitrosobenzene and phenothiazine.

Examples 13 and 14

Inhibition of Polymerization of Heated Liquid Acrylic Acid Monomer

General procedure: seal a vial containing liquid mixture of acrylic acid, 100 ppm of nitrosobenzene, and either Example 13a: 100 ppm of 4-hydroxy-TEMPO and 10 ppm of manganese acetate; or Example 14b: 100 ppm of N-(1-phenylethyl)-phenothiazine and 10 ppm of manganese acetate. Heat the vial at 113 C. Record time to the visual appearance of solid poly(acrylic acid) in the liquid mixture or on wall of vial above the liquid mixture. Repeat 4 times as Examples 13b to 13e and Examples 14b to 14e, respectively. Results are shown in Table 3.

TABLE 3 time to visual appearance of solid poly(acrylic acid)

| Example Number | Captive polymerization inhibitor | Time to visual appearance of solid poly(acrylic acid) (hours) |
|---|---|---|
| 13a | 4-hydroxy-TEMPO and manganese acetate | 105* |
| 13b | Same as 13a | 109* |
| 13c | Same as 13a | 111 |
| 13d | Same as 13a | 125* |
| 13e | Same as 13a | 131 |
| 14a | N-(1-phenylethyl)-phenothiazine and manganese acetate | 122* |
| 14b | Same as 14a | 180* |
| 14c | Same as 14a | 245* |
| 14d | Same as 14a | 400 |
| 14e | Same as 14a | >500 |

*Solid poly(acrylic acid) formed on wall of vial above the liquid mixture

Example 15

Distillation of Acrylic Acid Monomer

Assemble an Oldershaw distillation unit by equipping a thermosiphon reboiler with a 5 tray 1 inch (2.5 centimeter) Oldershaw tray section. Place a vapor side stream take-off section on top of the 5 tray section and attach a 10 tray section to the top of the vapor side stream section. Attach a feed section with feed preheater to the top of the 10-tray section. Top the column with an overhead take-off section with condenser and receiver. Fit the vapor side stream take-off with uninsulated glass tubing, which connects the column to the condenser and receiver. This glass tubing serves to act as a cold spot and significant condensation occurs and condensate forms on the walls of the glass tubing. Connect a line with an adjustable needle valve from the overhead receiver head space to the side stream receiver head space. The adjustable needle valve can be adjusted to control the rate of vapor removal from the column at the vapor side stream section. Equip both the overhead receiver and vapor side stream receiver with an FMI pump to allow liquid removal from the receivers. Equip a reboiler with a condenser and pump to remove residue from the column base. Feed liquid to the column using an FMI pump that is attached to the preheater of the feed section. Feed inhibitor solution (4-hydroxy-TEMPO and manganese acetate tetrahydrate) to both the overhead and vapor side stream condensers at the rate of 0.1 mL/minute. Electrically trace and insulate the overhead take-off section to prevent any condensation in the line prior to entering the condenser. Feed to the column an aqueous solution of acrylic acid which contains 100 ppm 4-hydroxy-TEMPO, 100 ppm nitrosobenzene, and 10 ppm manganese acetate tetrahydrate. Run the column for 4 hours, and then take a 30 minute mass balance. Repeat this experiment 4 times. During each operation time no polymer is formed in the uninsulated glass line or any where else in the system.

For comparison, repeat the experiments without using nitrosobenzene. Operation without the nitrosobenzene results in fouling within 30 minutes.

As shown by the above data, the composition of the first embodiment is useful in manufacture, purification, handling, and storage of distillable monomers, especially acrylic acid-type monomers, as an inhibitor of polymerization of the distillable monomers, especially acrylic acid-type monomers in, e.g., vessels and piping. The above data further show that at least preferred compositions of the first embodiment are further useful as inhibitors of distal-sited polymerization of evaporated and condensed acrylic acid-type monomers on structures, including distal structures, in the headspaces of, e.g., vessels and piping, and in columns (e.g., distillation columns), by way of the fugitive polymerization inhibitor. The data also show that the captive polymerization inhibitors (e.g., 4-hydroxy-TEMPO and manganese acetate or N-(1-phenylethyl)-phenothiazine and manganese acetate) also inhibit in situ conversion of the fugitive polymerization inhibitors (e.g., nitrosobenzene) to other captive polymerization inhibitors (e.g., phenylnitroxide), and allow condensing of the second polymerization inhibiting amounts of the evaporated fugitive polymerization inhibitors (e.g., nitrosobenzene) together with evaporated acrylic acid-type monomers (e.g., acrylic acid) at second locations (e.g., distal structures) and inhibiting polymerization of the evaporated and condensed acrylic acid-type monomers at the second locations (e.g., distal structures).

While the present invention has been described above according to its preferred aspects or embodiments, it can be modified within the spirit and scope of this disclosure. This application is therefore intended to cover any variations, uses, or adaptations of the present invention using the general principles disclosed herein. Further, the application is intended to cover such departures from the present disclosure as come within the known or customary practice in the art to which this present invention pertains and which fall within the limits of the following claims.

What is claimed is:

1. A distillable-monomer polymerization inhibitor composition comprising a liquid mixture comprising a distillable monomer, a captive polymerization inhibitor and a fugitive polymerization inhibitor, wherein:

the distillable monomer is an acrylic acid-type monomer of formula (M):

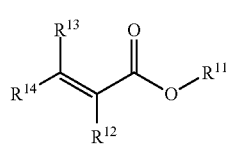

wherein $R^{11}$ is hydrogen or $(C_1\text{-}C_{18})$alkyl and each of $R^{12}$ to $R^{14}$ independently is hydrogen or $(C_1\text{-}C_8)$alkyl;

the captive polymerization inhibitor comprises a mixture of molecular oxygen and phenothiazine, or an acid addition salt thereof, and is present in an amount of from 5 parts per million to 500 parts per million of the liquid mixture;

the captive polymerization inhibitor and the fugitive polymerization inhibitor are different and not interconvertible between one another;

each of the fugitive polymerization inhibitor and the captive polymerization inhibitor independently is characterizable as being an inhibitor of polymerization of the distillable monomer; and the fugitive polymerization inhibitor is characterizable as being capable of evaporating with the distillable monomer from a first location and condensing with the distillable monomer at a second location that is different than the first location during distillation of the distillable monomer, wherein the fugitive polymerization inhibitor comprises nitrosobenzene and is present in an amount of from greater than 25 parts per million to 2000 parts per million of the liquid mixture; and wherein the acrylic acid-type monomer of formula (M) and the fugitive polymerization inhibitor are characterized by either (i) respective first and second liquid vapor pressures of substantially pure forms thereof or (ii) relative volatility of a test mixture consisting essentially of the acrylic acid-type monomer of formula (M), the fugitive polymerization inhibitor, and the captive polymerization inhibitor, wherein the first and second liquid vapor pressures are independently determined at a same elevated temperature, the elevated temperature being 50 degrees Celsius or higher, and the first liquid vapor pressure and the second liquid vapor pressure independently are at least 5 kiloPascals and are within 40 kiloPascals of each other; and the relative volatility of the test mixture is from 0.5 to 10.

2. The composition as in claim 1, wherein the acrylic acid-type monomer of formula (M) and the fugitive polymerization inhibitor are characterized by (i) respective first and second liquid vapor pressures of substantially pure forms thereof, wherein the first and second liquid vapor pressures are independently determined at a same elevated temperature, the elevated temperature being 50 degrees Celsius or higher, and the first liquid vapor pressure and the second liquid vapor pressure independently are at least 5 kiloPascals and are within 40 kiloPascals of each other.

3. The composition as in claim 1, wherein the nitrosobenzene is present in an amount of from greater than 50 parts per million to 200 parts per million of the liquid mixture.

4. The composition of claim 1, wherein the captive polymerization inhibitor further comprises a manganese salt that is $Mn(HCO_2^-)_2$, $Mn((C_1\text{-}C_8)\text{alkyl}CO_2^-)_2$, or potassium permanganate.

5. The composition of claim 4, wherein the manganese salt is manganese(II) acetate.

6. The composition of claim 1, wherein the captive polymerization inhibitor further comprises a mixture of an N-oxyl compound and a manganese salt that is $Mn(HCO_2^-)_2$, $Mn((C_1\text{-}C_8)\text{alkyl}CO_2^-)_2$, or potassium permanganate, optionally wherein the N-oxyl compound is 4-hydroxy-2,2,6,6-tetramethylpiperidine-1-oxyl.

7. The composition of claim 1, wherein the phenothiazine is present in an amount of from 10 parts per million to 250 parts per million of the liquid mixture.

8. The composition of claim 1, wherein the captive polymerization inhibitor further comprises a mixture of molecular oxygen and a compound of formula (II):

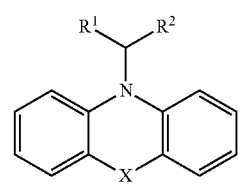

or an acid addition salt thereof,
wherein X is S, O, or N—$R^3$;
$R^1$ is hydrogen or $(C_1\text{-}C_3)$alkyl;
$R^2$ is phenyl; and
$R^3$ is $(C_1\text{-}C_3)$alkyl.

9. The composition of claim 8, wherein X is S.

10. The composition of claim 8, wherein $R^1$ is hydrogen.

11. The composition of claim 8, wherein $R^1$ is $(C_1\text{-}C_3)$alkyl.

12. The composition of claim 8, wherein $R^1$ is methyl.

13. The composition of claim 1, wherein the distillable monomer is acrylic acid.

14. The composition of claim 1, wherein the acrylic acid-type monomer of formula (M) and the fugitive polymerization inhibitor are characterized by (ii) relative volatility of a test mixture consisting essentially of the acrylic acid-type monomer of formula (M), the fugitive polymerization inhibitor, and the captive polymerization inhibitor, wherein the relative volatility of the test mixture is from 0.5 to 10.

15. The composition of claim 1, wherein the captive polymerization inhibitor further comprises hydroquinone.

16. A method of inhibiting polymerization of a distillable monomer during a distillation thereof, wherein the distillable monomer is an acrylic acid-type monomer of formula (M):

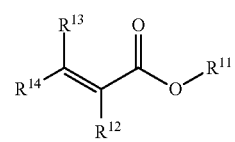

wherein $R^{11}$ is hydrogen or $(C_1\text{-}C_{18})$alkyl and each of $R^{12}$ to $R^{14}$ independently is hydrogen or $(C_1\text{-}C_8)$alkyl, the method comprising steps of:

(a) contacting together a distillable-monomer polymerization inhibitor composition and an amount of the distillable monomer to give a liquid mixture thereof at a first location, wherein the composition comprises a first polymerization inhibiting amount of a fugitive polymerization inhibitor and an inhibiting amount of a captive polymerization inhibitor, wherein the captive polymerization inhibitor and the fugitive polymerization inhibitor are different, not interconvertible between one another, and each of the fugitive polymerization inhibitor and the captive polymerization inhibitor independently is characterized as being an inhibitor of polymerization of the distillable monomer, and wherein the captive polymerization inhibitor comprises a mixture of molecular oxygen and phenothiazine, or an acid addition salt thereof, and is present in an amount of from 5 parts per million to 500 parts per million of the liquid mixture;

(b) evaporating from the first location at least some of the distillable monomer and at least some of the fugitive polymerization inhibitor to respectively give an evaporated distillable monomer and an evaporated fugitive polymerization inhibitor; and (c) condensing together at least some of the evaporated distillable monomer and at least some of the evaporated fugitive polymerization inhibitor to give a condensate mixture thereof at a second location that is different than and in fluid communication with the first location, wherein the condensate mixture comprises some of the amount of the distillable monomer and a second polymerization inhibiting amount of the fugitive polymerization inhibitor;

wherein polymerization of the distillable monomer at the second location is inhibited by the second polymerization inhibiting amount of the fugitive polymerization inhibitor; in and under conditions of distilling steps (b) and (c), the fugitive polymerization inhibitor has a vapor pressure or relative volatility distillation performance compatible with a vapor pressure or relative volatility distillation performance of the distillable monomer; and the fugitive polymerization inhibitor comprises nitrosobenzene and is present in an amount of from greater than 25 parts per million to 2000 parts per million of the liquid mixture.

17. The method of claim 16, wherein the captive polymerization inhibitor further comprises: a manganese salt that is $Mn(HCO_2^-)_2$, $Mn((C_1\text{-}C_8)alkylCO_2^-)_2$, or potassium permanganate; a mixture of an N-oxyl compound and a manganese salt that is $Mn(HCO_2^-)_2$, $Mn((C_1\text{-}C_8)alkylCO_2^-)_2$, or potassium permanganate; hydroquinone; a compound of formula (II):

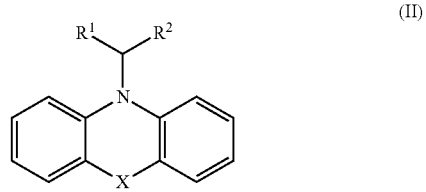

or an acid addition salt thereof,
wherein X is S, O, or N—$R^3$; $R^1$ is hydrogen or ($C_1$-$C_3$) alkyl; $R^2$ is phenyl; and $R^3$ is ($C_1$-$C_3$)alkyl;
or a combination of any two or more captive polymerization inhibitors of the foregoing.

18. The method of claim 16, wherein the nitrosobenzene is present in an amount of from greater than 50 parts per million to 200 parts per million of the liquid mixture.

19. The method of claim 16, wherein the phenothiazine is present in an amount of from 10 parts per million to 250 parts per million of the liquid mixture.

20. The method of claim 16, wherein the distillable monomer is acrylic acid.

* * * * *